United States Patent [19]
Takeuchi

[11] Patent Number: 5,271,734
[45] Date of Patent: Dec. 21, 1993

[54] LIGHT-EMITTING DENTAL PROBE FOR MEASURING GUM POCKETS

[76] Inventor: Hideyuki Takeuchi, 9-41 Kyomachi, Fushimi-ku, Kyoto-city, Kyoto-Pref., Japan

[21] Appl. No.: 769,875
[22] Filed: Oct. 1, 1991
[51] Int. Cl.⁵ .............................................. A61C 19/04
[52] U.S. Cl. ........................................ 433/72; 433/29
[58] Field of Search ...................... 433/72, 29; 33/513, 33/514

[56] References Cited

U.S. PATENT DOCUMENTS

| | | | |
|---|---|---|---|
| 4,501,555 | 2/1985 | Ditchburn | 433/72 |
| 4,790,751 | 12/1988 | Reinhardt et al. | 433/29 |
| 4,886,454 | 12/1989 | Loewenthal et al. | 433/72 |
| 5,022,856 | 6/1991 | Zimble | 433/72 |

FOREIGN PATENT DOCUMENTS

| | | | |
|---|---|---|---|
| 8403143 | 8/1984 | PCT Int'l Appl. | 433/72 |
| 8808956 | 11/1988 | PCT Int'l Appl. | 433/72 |

Primary Examiner—John J. Wilson
Attorney, Agent, or Firm—Poms, Smith, Lande & Rose

[57] ABSTRACT

A measuring device for measuring the depth of a blind pocket formed around a tooth. A first embodiment of the measuring device has a measuring probe of optical material, such an optical fiber or rod, that has light-emitting notches or grooves near the probe tip, the notches being spaced to form a rule. The probe can be coupled to a light source, such as a penlight which can also be used as handle. The measuring probe is provided with an optical path to conduct light from the light source to the light-emitting ruler markings. A second embodiment of the measuring device has a measuring probe with a tapered tip formed by a staircase bundle of optical fibers covered by a transparent sheath. When light is introduced into a light source end of the staircase bundle of optical fibers, the opposite end in the probe's tapered tip is illuminated in a staircase pattern that can be used as rule.

18 Claims, 1 Drawing Sheet

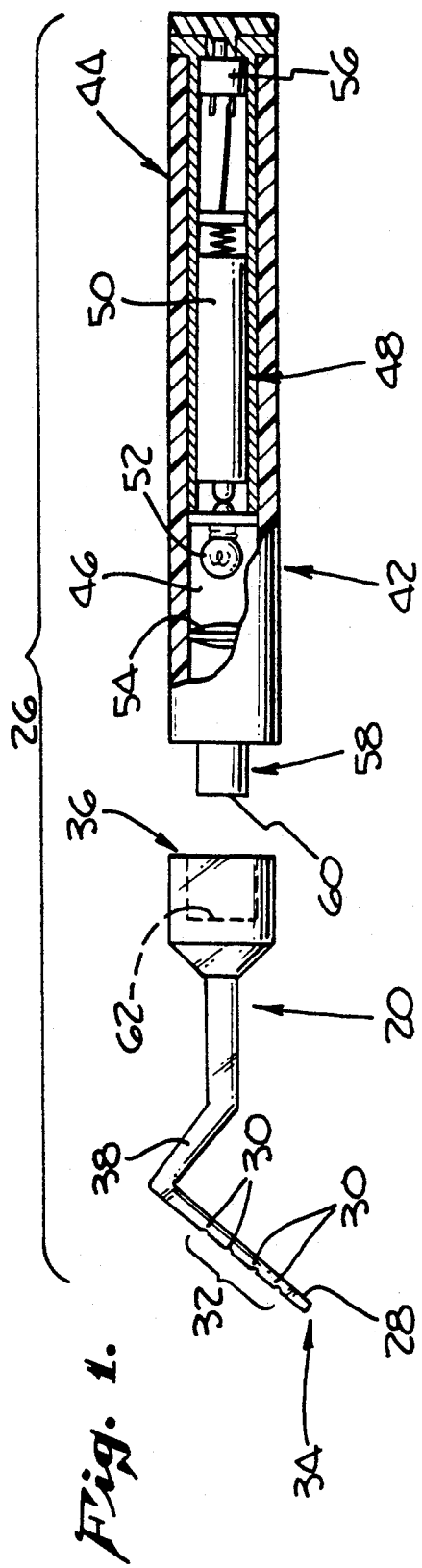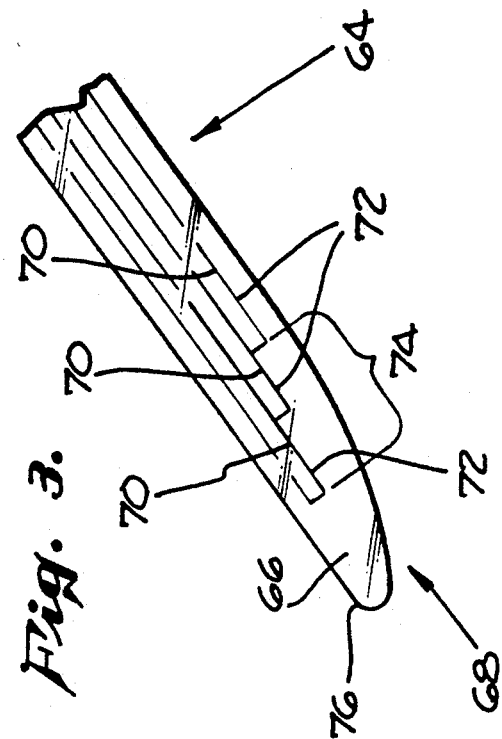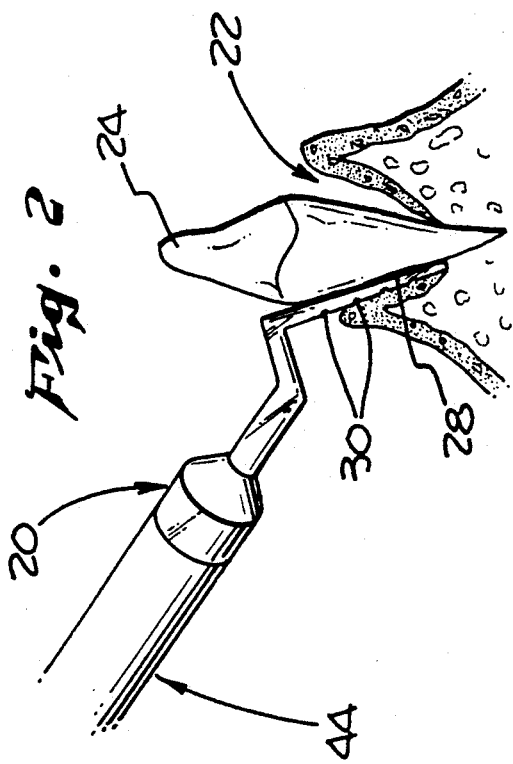

LIGHT-EMITTING DENTAL PROBE FOR MEASURING GUM POCKETS

FIELD OF THE INVENTION

The present invention relates to dental devices and more specifically to a dental tool for measuring the depth of blind pockets that form around teeth during periodontal disease.

DESCRIPTION OF RELATED ART

When a person is afflicted with a periodontal disease and gum inflammation progresses, blind pockets form around his teeth. If it progresses too far, inflammation in a deep part of the mouth will arise, destroying the paradentium, which then must be treated.

For treatment it is necessary to measure the depth of the blind pockets to determine the course of the gingivitis. Dentists and their assistants use many techniques and medical devices to measure blind pockets. One measuring tool is a metal rod having a head, with a thin, doglegged metal measuring needle attached thereto.

Graduations such as 3 mm, 3 mm, 2 mm and 2 mm are etched on the measuring needle of the head. When the tip of this measuring needle is inserted into the blind pocket, the pocket's depth can be measured by observing which gradations remain visible. However, this device and method do not give accurate measurements because the needle tip cannot be accurately positioned at the bottom of the blind pocket. Furthermore, because the patient's mouth cavity is dark, it is difficult for the user to see the fine gradation cuts on the thin needle.

Moreover, if not used with care, such tools can injure the patient. The tool's thin metal needle tip can easily puncture and wound the patient's gum when inserted into the affected area and if the needle is unsterilized there is danger of transmitting a contagious diseases, such as AIDS.

Accordingly, it is an object of the preset invention to provide a dental measuring device for treating periodontal diseases that will not damage the gum or transmit contagious diseases.

A further object is to provide a dental measuring device that also illuminates the dark mouth cavity.

Yet another object is to provide a dental measuring device enabling very accurate measurements of the depth of a blind pocket.

SUMMARY OF THE INVENTION

These and other objects are achieved according to the present invention by providing a measuring probe adapted to emit light from a light source, enabling safe use and accurate measurements of gum pockets, etc.

More specifically, the measuring portion has preselected spacing indicators to emit light provided by a light source. The preselected spacing indicators are cut, notched, grooved, or in some other way formed, to allow light to escape from the measuring portion of the probe to illuminate the mouth cavity and area around a tooth. The preselected spacing indicators are then an easily visible rule for measuring the depth of a blind pocket.

To measure the depth of a blind pocket with the improved tool, the user first carefully inserts the needle tip, taking notice of the position, number, strength and color of the light released from the exposed cuts on the needle. To improve the visibility of the light passing through the cuts, the cuts can be painted or otherwise given various colors so preselected colors are released through the measuring cuts.

To enable light to pass through the cuts and other parts of the probe's measuring portion, the probe is preferably made of optical plastic or another relatively elastic and soft light-transparent material, and includes or is formed of an optical conductor such as optical fiber. Inorganic glass can be used as the optical fiber, but plastic fiber is preferable because of its moderate elasticity and easy handling. Whatever optical fiber is used, the probe is designed for optical coupling to a light source.

Any suitable light source can be used. For example, a penlight, having of a battery and miniature bulb can be used. Such a small light source can be incorporated in a grip adapter or handle which is mechanically and optically coupled to the measuring probe. A switch can be provided in the bulb-battery circuit to turn the bulb on and off, and the manually-operated portion of the switch can be set on the outside of the handle.

Alternative light sources include a soft laser light generator of the type adapted for dental treatment or a halogen lamp, which can be optically coupled to the probe by an optical fiber lead. Such an optical fiber lead can be set into the handle so the light from the laser or lamp is conducted into the probe's optical fiber needle. If a soft laser is used, the laser light may also be used to treat a deeply affected part in the mouth.

A recording device to receive light can be fit onto the appliance. The light emitted from the measuring needle can be sensed quantitatively by the device and transmitted to an automatic recording device, such as a computer.

The head of the measuring probe must internally conduct light and have openings or cuts that release the light conducted to it by the optical fiber needle. It is preferable to fit the opening of the handle which passes light to the probe with a lens in order to concentrate the light.

The measuring probe and handle are coupled in a secure yet easily removable way. Generally, fastening by a thread screw couple is better than a capping arrangement. The use of a threaded screw couple is secure yet allows for easy removal of the measuring portion and the handle. An easily removable measuring portion is needed so after just one use it can discarded and replaced with a sanitary new one.

BRIEF DESCRIPTION OF THE DRAWINGS

FIG. 1 is a side elevation view of a first embodiment of a measuring probe according to the invention, together with a partial sectional view of a mating grip portion.

FIG. 2 is an enlarged view showing the needle tip of the measuring probe of FIG. 1 inserted for measurement in a blind pocket formed around a tooth.

FIG. 3 is an enlarged cross sectional view showing a second embodiment of a fiber optic needle tip.

DETAILED DESCRIPTION O THE DRAWINGS

As shown in FIG. 1, an improved measuring probe 20 enables a safer and more accurate measurement (FIG. 2) of blind pockets 22 formed around a tooth 24. This invention presents a measuring device 26 more advantageous than previous measuring assemblies.

As shown in FIG. 2, the measuring device is used by first inserting measuring probe 20, and more specifically a light emitting tip 28, into gum pocket 22 (FIG. 2). Light emitting tip 28 has a plurality of notches or grooves 30 that allow light to exit the probe, thereby providing an easily visible rule 32 for measuring the depth of blind pocket 22. Notches 30 also illuminate the mouth cavity and the area around tooth 24. Because of the light exiting notches 30, the user can easily see which notches 30 remain exposed, enabling accurate measurement of the pocket depth. Since the mouth cavity is illuminated, the user can see where he is inserting the light emitting tip 28 and will not place the tip where it can injure the patient.

As shown in FIGS. 1 and 2, probe 20 has a distal end 34 and a proximal end 36. Measuring probe 20 further includes a light emitting tip 28 on distal end 34. Light emitting tip 28 is made of an fiber optic material 38 or some other suitable elastic material, such as a light emitting plastic. Light emitting tip 28 has preselected spacing indicators 30, such as notches or grooves, of a predetermined spacing, that allow light within the probe to exit. This makes these preselected spacing indicators 30 easy to see and can also illuminate the mouth cavity and the area around tooth 24.

The optical fiber or tube used in probe 20 is made of an optically denser than air medium, such as glass or plastic. Light entering one end of the fiber travels longitudinally along the fiber, undergoing total internal reflection at the lateral walls of the fiber. However, if a notch or groove 30 is made in the wall of an optical fiber or tube, some of the longitudinally traveling light rays will impinge on the wall of notch 30 at an angle of incidence which causes such light rays to instead be refracted out of the fiber or tube. Hence, the notch 30 will emit a portion of the light traveling along the fiber or tube.

Notches 30 are suitably spaced, such as at equal intervals, so they can be used as a rule 32 when measuring the depth of blind pocket 22. The light emitted from notches 30 enables the user to see the number of notches that remain exposed so he can accurately determine the depth of blind pocket 22. To make it even easier for the user to observe notches 30, one or more of the notches can be colored by a colored coating.

The light source 42 that transmits light to light emitting tip 28 can be any convenient light source, such as a penlight 48. As shown in the preferred embodiment of FIG. 1, light source 28 can be incorporated in a handle 44 (FIG. 1) which is mechanically and optically coupled to measuring probe 20. Handle 44 has a housing chamber 46 for the light source, such as a battery powered penlight. Penlight 48 includes a battery 50, such as a dry cell, or other electric power source, electrically connected to a light bulb 52. A lens 54 (partially shown) can be provided in chamber 46 to concentrate the light from light bulb 52, directing it towards the probe. A switch 56 to turn the light bulb 52 on and off can be mounted on the outside of the handle. Other suitable light sources are a laser or a halogen light source (not shown), optically coupled to measuring probe 20 by an optical fiber or the like.

Measuring probe 20 and handle 44 are coupled by a threaded coupling 58. A threaded screw couple 60 is used to couple these parts. Threaded screw couple 60 is preferred because it enables a secure fit yet allows easy disassembly of the two parts. Easy disassembly is desirable because once the light emitting tip becomes contaminated it should be discarded and replaced with a fresh one.

Measuring probe 20 and handle 44 are formed to mate with each other in a secure manner. Measuring probe proximal end 36 has a cap 62 or other coupling designed to mate with an end portion of handle 44.

An enlarged view of a second embodiment of a measuring device 64 is shown in FIG. 3. This device has a measuring probe 66 having a distal end 68 and a proximal end (not shown). Measuring device 64 has a core of optical fibers and can be adapted for coupling to a light source as in the first embodiment of FIG. 1. The distal end 68 of probe 66 is tapered, the taper being formed by a staircase bundle of optical fibers 70, the ends of the fibers of the bundle protruding in steps towards distal end 68 as shown in FIG. 3. The staircase of optical fibers can have steps 72 of equal length at the measuring probe distal end 68. When light is introduced into the other end (not shown) of the bundle of optical fibers, the staircase of steps 72 of optical fibers ends will become easily distinguishable, even in a dark mouth cavity. When probe 66 is inserted into a gum pocket 22, steps 72 can be used as rule 74 for measuring the depth of the gum pocket 22.

A transparent sheath or cover 76 can be provided on distal end 68 to smoothly envelop the staircase bundle of optical fibers 70. When the tip of probe 66 is inserted into a gum pocket, transparent sheath 76 provides a smooth tip yet enables the user to see what portion of staircase rule 74 is not covered by the gum, and thus to measure the depth of the gum pocket.

Measuring device 66 can be for attachment to, or include, a handle having a housing chamber for a light source. The handle can be similar to the handle described for the first embodiment of FIG. 1. The laser and halogen light sources can also be used.

Although the present invention has been described in detail with reference only to the present preferred embodiments, it will be appreciated by those of ordinary skill in the art that various modifications can be made without departing from the spirit of the invention. Accordingly, the invention is limited only by the following claims.

What is claimed is:

1. A measuring device for measuring the depth of a gum pocket formed around a tooth, comprising;
   a measuring probe having a distal end and a proximal end;
   a light emitting tip on said measuring probe's distal end, having a plurality of preselected spacing indicators;
   means for transmitting visible light through said preselected spacing indicators, at least one of the spacing indicators having means for coloring the visible light transmitted through it a different color from the visible light transmitted through one of the other spacing indicators; and
   means for illuminating an area around a tooth with visible light.

2. The measuring device of claim 1 wherein said means for transmitting light through said preselected spacing indicators is optically coupled to a light source comprising a handle having chamber means for housing a battery electrically connected to a light bulb.

3. The measuring device of claim 2 further comprising coupling means for mechanically and optically coupling said measuring probe and said light source.

4. The measuring device of claim 3 wherein said coupling means comprises a threaded coupling.

5. The measuring device of claim 4 wherein said coupling means comprises a screw.

6. The measuring device of claim 2 wherein said measuring probe's proximal end includes means for mating with said light source.

7. The measuring device of claim 1 wherein said means for transmitting light through said preselected spacing indicators is optically coupled to a laser light source.

8. The measuring device of claim 1 wherein said means for transmitting light through said preselected spacing indicators is optically coupled to a halogen light source.

9. The measuring device of claim 1 wherein said measuring probe comprises a fiber optic material.

10. The measuring device of claim 1 wherein said preselected spacing indicators are equally spaced.

11. The measuring device of claim 1 wherein said preselected spacing indicators are light emitting notches in said light emitting tip.

12. The measuring device of claim 11 wherein at least one of said notches is colored.

13. A measuring device for measuring the depth of gum pockets, comprising:
   a measuring probe having a tapered distal end and a proximal end, said measuring probe comprising a staircase bundle of optical fibers forming the taper on said measuring probe's distal end;
   a sheath encapsulating said staircase bundle of optical fibers; and
   a source of visible light optically coupled to the measuring probe.

14. The measuring device of claim 13 wherein said staircase bundle of optical fibers has a staircase of equal steps.

15. The measuring device of claim 13 wherein said sheath is transparent.

16. The measuring device of claim 13 further including a handle, and a light source enclosed in the handle.

17. The measuring device of claim 13 further including means for optically coupling said measuring probe to a laser light source.

18. The measuring device of claim 13 further including means for optically coupling said measuring probe to a halogen light source.

* * * * *